United States Patent [19]

Evans, Jr.

[11] 4,341,109
[45] Jul. 27, 1982

[54] METHOD AND APPARATUS FOR DETERMINING CIGARETTE FILTER ROD PRESSURE DROP

[75] Inventor: John D. Evans, Jr., Kingsport, Tenn.

[73] Assignee: Eastman Kodak Company, Rochester, N.Y.

[21] Appl. No.: 166,626

[22] Filed: Jul. 7, 1980

[51] Int. Cl.³ .............................................. G01B 13/08
[52] U.S. Cl. ........................................ 73/37; 73/37.5; 73/38; 356/387
[58] Field of Search ........................... 73/37, 37.5, 38; 356/387

[56] References Cited

U.S. PATENT DOCUMENTS

| | | | |
|---|---|---|---|
| 3,668,928 | 6/1972 | Strydom | 73/38 X |
| 3,955,406 | 5/1976 | Strydom | 73/37.5 X |
| 4,069,704 | 1/1978 | Grant, Jr. et al. | 73/38 |
| 4,155,248 | 5/1979 | Wagner et al. | 73/38 |
| 4,213,707 | 7/1980 | Evans, Jr. | 356/387 |

FOREIGN PATENT DOCUMENTS 1372056 10/1974 United Kingdom ................ 73/37

Primary Examiner—Kyle L. Howell
Assistant Examiner—Joseph W. Roskos
Attorney, Agent, or Firm—Malcolm G. Dunn; Daniel B. Reece, III

[57] ABSTRACT

Method and apparatus for determining true cigarette filter rod pressure drop, especially of nonwrapped and soft wrapped filter rods when the circumference thereof is being compressed by an encapsulation method as by an elastic sleeve, the pressure drop and circumference of the elastic sleeve and the filter rod encapsulated therewithin being measured simultaneously, and then through a fifth power relation true pressure drop is determined.

6 Claims, 5 Drawing Figures

METHOD AND APPARATUS FOR DETERMINING CIGARETTE FILTER ROD PRESSURE DROP

DESCRIPTION

Technical Field

My invention is directed to a method by which substantially true pressure drop of nonwrapped and soft wrapped cigarette filter rods may be determined when the circumference of such cigarette filter rods is being compressed for such determination by a total encapsulation procedure of the entire filter rod, and to an apparatus for practicing the method. The apparatus is adapted for use with gauging instruments such as optical measuring apparatus, which measure dimensional parameters of articles by scanning the surface or main profile of the article with a light beam as from a laser.

BACKGROUND

The pressure drop of cigarette filter rods, or resistance to air flow through the filter rod, is one of the primary physical properties which must be controlled in order to produce quality cigarettes. Since the pressure drop of filter rods is directly related to filtration efficiency, the tobacco industry needs assurance that accurate measurements can be made on the particular filter rods being manufactured.

"Pressure drop" involves measuring the pressure difference between the two ends of the tested filter rod, when air or other gas is drawn through it at a given flow rate. The flow rate is conventionally 17.5 milliliters per second measured at exit end of filter rod, and the air or gas may be aspirated or blown through the filter rod.

Generally, pressure drop of conventional filter rods wrapped with non-porous plugwrap has been tested on a variety of pressure drop sensing devices, using both forced air and vacuum systems. The increased use of porous plugwrap, however, has necessitated the need for totally encapsulating these filter rods with an elastic sleeve or a rubber diaphragm arrangement to prevent air leakage problems. It has been found that the pressure drops of filter rods made with the same denier per filament and total denier tow and at the same circumference and length but wrapped with paper of different porosities will vary according to the porosity of the paper. The filter rods wrapped with the less porous paper will have a higher pressure drop than the filter rods wrapped with the more porous paper. Therefore, total encapsulation of the filter rod for testing pressure drop eliminates the factor of the porosity of the paper.

A soft wrapped filter rod is one which may have a lower total denier of tow, or smaller denier per filament or a lower amount of plasticizer content, any or all of which determines the hardness or softness of a paper wrapped filter rod. A paper wrapped filter rod of sufficient hardness is normally not significantly compressed in a total encapsulation procedure.

Nonwrapped cigarette filter rods, such as nonwrapped cellulose acetate filter rods (NWA) present a different problem in accurately measuring pressure drop because without the paperwrap the elastic sleeve or rubber diaphragm actually compresses the wrapless filter and thus causes an overstatement of the pressure drop. One well-known method for testing pressure drop of nonwrapped filter rods involves inserting 50 millimeters of a filter rod into a steel tube of known inside diameter and then measuring the pressure drop by inserting the tube into a conventional pressure drop measuring apparatus. This latter method, however, has been found to be vulnerable to air leakage between the peripheral surface of the filter rod and the inside peripheral surface of the tube.

When a nonwrapped or soft wrapped filter rod is totally encapsulated the resulting compression increases pressure drop reading. A tobacco manufacturer cannot determine, therefore, the yield of the filter rod, the "yield" being a relative measure of the amount of tow required to produce a given or desired pressure drop.

DISCLOSURE OF INVENTION

In accordance with the present invention, therefore, I have found that if the pressure drop and circumference of the cigarette filter rod are measured simultaneously, then one knows at what circumference the filter rod pressure drop was read while being compressed inside an elastic sleeve or rubber diaphragm. The resulting circumference measurement may then be used in a fifth power relation to determine substantially true pressure drop of the filter rod, as though the filter rod were in the uncompressed state when such reading was taken. I have therefore developed a method for making these measurements simultaneously, and an apparatus for practicing the method.

My invention thus concerns a method by which substantially true pressure drop measurement of nonwrapped and soft wrapped filter rods may be determined when the circumference of the filter rods is compressed for such measurement by an encapsulation method or procedure. The method involves encapsulating the entire length of a filter rod in a gas impervious elastic sleeve, applying by such elastic sleeve a predetermined compression of the circumferential surface of the filter, and conforming the elastic sleeve in close sealing adherence to the surface of the circumferential profile of the filter rod to form a substitute profile on the profile of the filter rod, the substitute profile thus providing a reference surface to be measured. A gas flow is then generated at a predetermined rate through the elastic sleeve and through the filter rod encapsulated therein, the pressure difference between the flow of gas entering and the flow of gas leaving the filter rod is measured, and the circumference of the substitute profile of the elastic sleeve is also measured. Preferably, the elastic sleeve and the filter rod encapsulated therewithin are rotated to obtain the substitute profile circumference measurement. From these measurements substantially true pressure drop is then determined in the manner described later in this specification.

The apparatus of the invention for practice of the method is adapted for use with a gauging instrument, which measures and indicates the circumference of articles by means scanning the surface of the articles, and serves to determine in cooperation with such gauging instrument substantially true pressure drop measurement of nonwrapped and soft wrapped filter rods when the circumference of the filter rods is compressed for such pressure drop measurement by an encapsulation method. The apparatus has an elastic sleeve arrangement for receiving therewithin the entire length of a filter rod, and is adapted to encapsulate the filter rod by close sealing adherence to and predetermined compression of the circumferential surface of the filter rod and thereby form a substitute profile on the profile of the filter rod, the substitute profile providing a reference surface to be measured. The elastic sleeve arrangement is suitably supported in the apparatus. Provision is made for generating a gas flow at a predetermined rate through the elastic sleeve and through the filter rod encapsulated in the elastic sleeve, and the pressure difference at the predetermined flow rate between the flow of gas entering and the flow of gas leaving the filter rod is measured and indicated. Provision is also made for rotating the elastic sleeve arrangement while the gauging instrument measures the substitute profile circumference. The arrangement for supporting the elastic sleeve includes at one end of the elastic sleeve an annular insertion guide defining an opening through which a filter rod is inserted therethrough and into the elastic sleeve, and also defining a radial outer surface around which the forward end of the elastic sleeve is sealingly attached. At the other end of the elastic sleeve there is an annular seat member against which the filter rod is seated while in the elastic sleeve and which defines a tapered radial outer surface around which the other end of the elastic sleeve is sealingly attached, and also defines an opening through which the gas flow passes. The tapered radial outer surface of the annular seat member is tapered to about the same diameter of the elastic sleeve, and the radial outer surface of the annular insertion guide has a diameter greater than that of the elastic sleeve and is spaced a predetermined distance from the filter rod so as to prevent pinching of the filter rod end. The purpose of these aforedescribed elements is to prevent the ends of the filter rod from being crushed, pinched or rounded, and thus resulting in an incorrect pressure drop reading.

The apparatus is designed to cooperate with a gauging instrument such as optical measuring apparatus which measure a dimension of an object or article without making physical contact with the article because they may use a scanning light beam from a light source, such as a laser, to make the desired measurement or measurements.

For instance, in U.S. Pat. No. 3,765,774, the disclosed optical measuring apparatus, with which the device of the present invention may be particularly suited to be used, has a laser light source which produces a narrow light beam having a diameter of approximately 1 millimeter. According to the description in the patent, the light beam is converted into a rotary scanning light beam by a mirror positioned within the path of the light beam at an angle of 45° and mounted on a flywheel driven by a synchronous motor. The motor receives a power supply from a high frequency pulse generator or clock through an adjustable frequency divider. The rotary scanning light beam is directed through a scanner lens which converts the rotary scanning light beam to a parallel scanning light beam, and the article to be measured is located at approximately the focal point of the lens where the diameter of the light beam is minimized. On the other side of the article to be measured, and also within the path of the light beam, is another lens, the receiver lens, which converges or focuses the parallel scanning light beam onto a photodetector, which produces pulses or signals when the light reaching the photodetector changes in intensity. The signals are amplified and transmitted to a decoder which incorporates means for selecting different combinations of the signals according to the dimension to be measured. The decoder transmits the selected signals to a gate which also receives the high frequency pulses from the clock, and the output of the gate is transmitted to a pulse counter calibrated so that each counted pulse represents a finite unit of length such as 0.0005 inch. The output of the pulse counter controls a digital readout display.

In brief, the parallel scanning light beam scans between two known reference points, and when an article is placed within the path of the parallel scanning light beam, the blackout time of the light beam, as sensed by the photodetector, corresponds precisely to the dimension of the article represented by the interruption of the parallel scanning light beam. In other words, the interrupted beam is collected by the receiver lens and focused onto a photodetector which converts the light signal to a time dependent signal. The time dependent signal is processed by appropriate electronic circuitry as shown in the patent, to give the desired read-out. The object or article to be measured may be stationary or moving.

In attempting to use laser scanning apparatus such as disclosed in U.S. Pat. No. 3,765,774 above, there is a loss of accuracy when measuring the circumference of porous wrapped tobacco smoke filter rods or when measuring diameters, circumferences, etc., of nonwrapped filter-type rods, for whatever their uses may be. This loss of accuracy occurs because of the surface fuzz associated with porous wraps and the nonwrapped cellulose acetate rods. A fuzzy surface on a filter rod tends to cause the optical measuring apparatus to overstate the circumference because the surface fibrils of the porous wrap project above the main profile of the filter rod. This situation was proved when a metal standard for the filter rod was used and then lint was applied to the surface of the metal standard. The optical measuring apparatus read higher than the actual metal standard value.

The elastic sleeve, therefore, provides a substitute profile that suppresses the surface irregularities projecting from the main profile of the nonwrapped or porous wrapped filter rod.

BRIEF DESCRIPTION OF DRAWINGS

The details of my invention will be described in connection with the accompanying drawing, in which.

BEST MODE FOR CARRYING OUT THE INVENTION

In reference to drawings, 10, designates an optical measuring instrument with which the apparatus 12 of my invention may be used to cooperate.

The optical measuring instrument 10 is disclosed in greater detail in the previously mentioned U.S. Pat. Nos. 3,765,774, 3,905,705 and 4,007,992, and the disclosures in these patents are herein incorporated by reference to the patents. It is deemed, therefore, sufficient to give only a brief description later of the functioning of the optical measuring instrument, as it operates in accordance with the invention.

Figure 1:
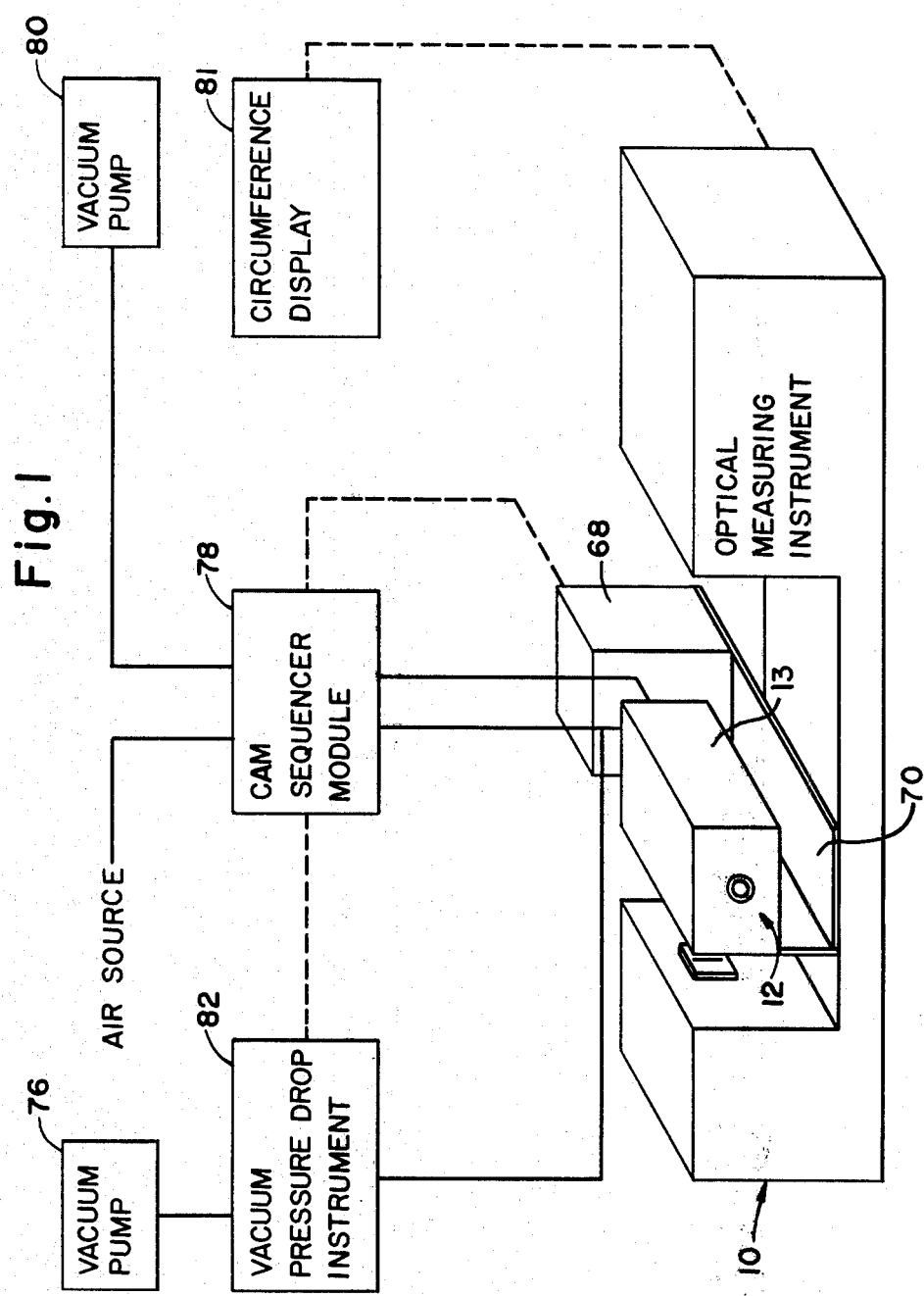
FIG. 1 is a diagrammatic illustration of apparatus constructed in accordance with the invention and including a vacuum pump for providing sensing air, a vacuum pressure drop instrument for receiving the sensing air and indicating pressure drop, a sealed chamber, a second vacuum pump for sequentially pulling a vacuum on the sealed chamber and for pulling a filter rod to the back of the sealed chamber, an optical instrument for measuring and indicating circumference of a filter rod in the sealed chamber, a motor drive for rotating a filter rod in the sealed chamber and a cam sequencer module for controlling the operation in proper sequence of the aforementioned components, with the solid lines between the components representing air lines, and the dotted lines representing electrical connections.
Figure 2:
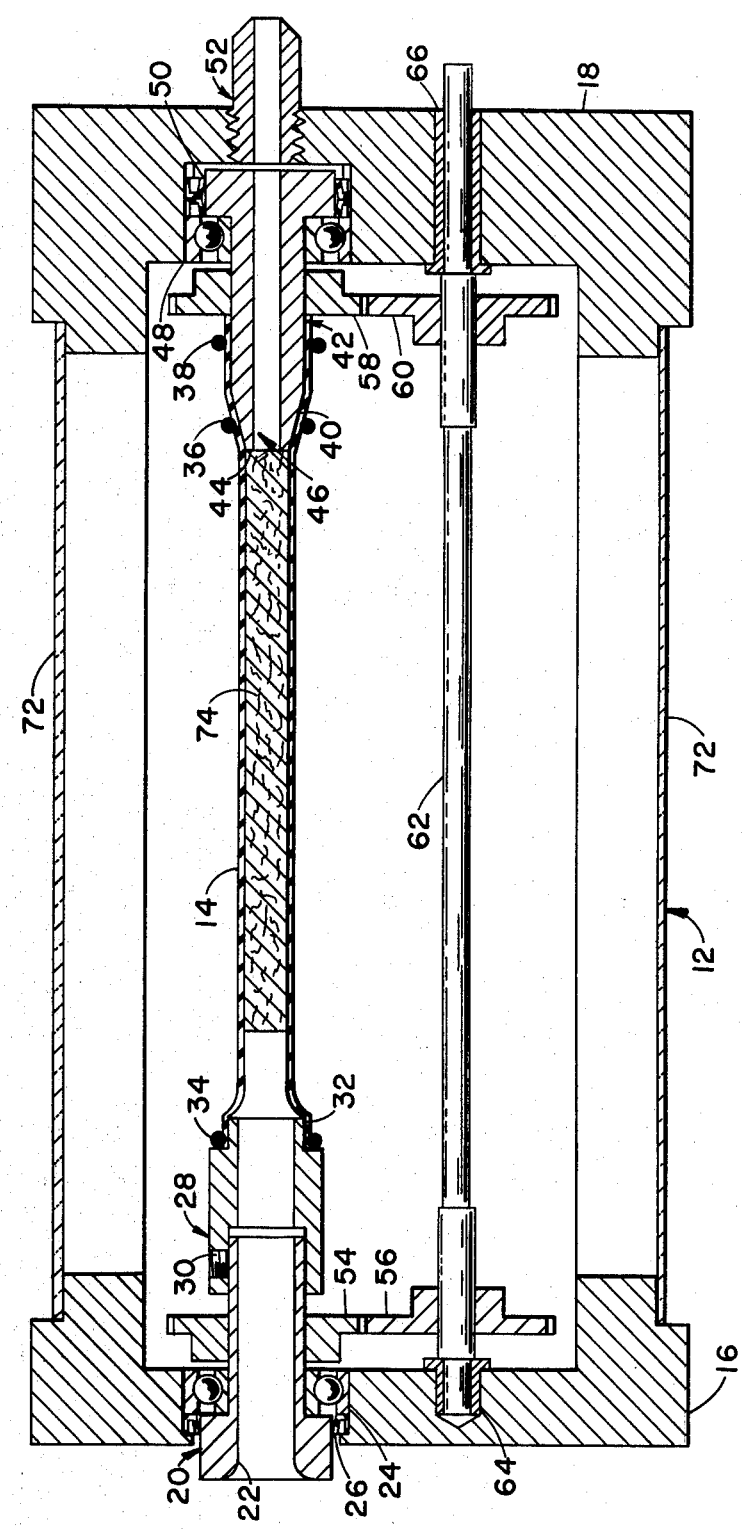
FIG. 2 is an enlarged elevational view in cross-section, taken along the axial length of the chamber.

The apparatus 12 includes a sealed chamber 13 within which and along part of the length thereof a tubular rubber diaphragm or elastic sleeve 14 is supported for rotation around its axis between the two end walls 16,18. At the forward end of the chamber, as viewed from FIG. 1 but with reference to FIG. 2, an annular insertion member 20 extends through end wall 14 and defines an opening 22 through which a cigarette filter rod may be inserted for receipt within the elastic sleeve. The annular insertion member is supported for rotation by ball bearings 24, and air or other gas is prevented from escaping past the annular insertion member 20 by the annular rubber seal 26, which is seated within the end wall 14.

The inner end of the annular insertion member 20 is reduced in diameter from the outer end portion and serves to provide a tubular surface upon and along which an annular member 28 is adjustably seated, as by set screw 30, for accommodating different lengths of filter rods. The axial inner end of the annular member is reduced in diameter to essentially the diameter of a cigarette filter rod to be tested, so as to prevent the end of the filter rod from being crushed or pinched by the elastic sleeve, and provides in turn an annular outer surface 32 around which one end or the forward end of the elastic sleeve 14 is sealingly connected, as by means of a rubber O-ring 34. The opposite or rearward end of the elastic sleeve 14 is sealingly connected via O-rings 36,38 to and around a tapered outer surface 40 of the back member 42. The forward end of the back member defines a seat 44 against which a filter rod is to abut when in seated position, and has a diameter essentially the same as that of the cigarette filter rod to be tested to prevent that end of the filter rod from being crushed or rounded by the elastic sleeve. The back member defines an opening 46 along the axial length of the back member through which air or other gas may flow.

The back member 42 is supported in end wall 18 for rotation around its axis by ball bearings 48. An annular rubber seal 50 is seated within end wall 18 to prevent flow of air or other gas past the back member 42.

Fitting 52 (to which a gas conduit may be connected) adjacent the outer end of the back member extends through the end wall 18 and defines an opening along and through its axis to form an outlet port through which air or other gas may be vented and ejection air may be supplied.

Both ends of the tubular rubber diaphragm or elastic sleeve 14 are designed to be rotated simultaneously together by gears 54,56 at one end and gears 58,60 at the other end, and drive shaft 62, which interconnects the two sets of gears. The drive shaft 62 is supported for rotation within the end walls 16,18 by journals 64,66, respectively. The drive shaft may be suitably connected to be driven by a drive motor 68, as represented by the box shown in FIG. 1.

The sealed chamber 13 may be suitably supported upon the optical measuring instrument 10 by means of a bracket support 70, and optical glass plates 72 are suitably sealed across and between the end walls 16,18 to enable the scanning laser beam from the optical measuring instrument to pass therethrough. The optical glass plates are slanted in their supports (not shown) at an angle of 6° from the vertical plane so as to avoid any undesirable reflection.

OPERATION

In operation of the apparatus, a cigarette filter rod 80 to be tested is inserted into the opening 22 through the annular insertion member 20. The vacuum pump 76 is first sequenced by the cam sequencer module 78 (Cam Sequence Module—8 Position—Type MP5A 611, manufactured by Eagle Signal Manufacturing Division, Baraboo, Wis., Division of Gulf & Western Inds., modified to run at six revolutions per minute) to pull a vacuum upon the sealed chamber 13 through a fitting and an opening not shown in FIG. 2, thereby causing the tubular rubber diaphragm or elastic sleeve 14 to become expanded, and then sequenced to pull a vacuum upon the outlet port of fitting 52 so as to cause the cigarette filter rod to be moved into seated position against seat 44 of the back member 42. The vacuum upon the sealed chamber is then sequenced for release, and as a consequence the elastic sleeve collapses around the cigarette filter rod to sealingly adhere to the circumferential surface of the filter rod and thus encapsulate it. The elastic sleeve now forms a substitute profile for the main profile of the cigarette filter rod and serves as a reference surface to be measured. The ends of the cigarette filter rod are protected from being rounded over or crushed by the elastic sleeve by means of the respective ends of the adjustable annular member 28 and back member 42, and spacing of the former from the filter rod, as previously described.

A second vacuum pump 76 (FIG. 1) is then sequenced by the cam sequencer module 78 to pull a flow of sensing air or other gas through the annular insertion member, the elastic sleeve and the sample cigarette filter rod. When a state of equilibrium is achieved, usually about 2 seconds, the cam sequencer module 78 causes the drive motor to be energized for rotating the elastic sleeve and the filter rod contained therein, so that the optical measuring instrument 10 can measure and give a reading indication at 81 of the circumference of the substitute profile, as formed by the elastic sleeve around the filter rod. At the same time the vacuum pressure drop instrument 82 is sequenced to sense and give a reading indication of the pressure drop of the air or gas flow between the two ends of the filter rod.

The first vacuum pump 80 is again sequenced to pull a vacuum upon the sealed chamber 13 so as to again cause a slight expansion of the elastic sleeve to release it from sealing engagement with the filter rod, and then a solenoid-activated jet (not shown, located in box representing cam sequencer module) of air is applied to the outlet port of fitting 52 to cause the filter rod to be ejected out through the annular insertion member 20.

The circumference of the elastic sleeve substitute profile is compensated for in the manner to be described so as to obtain the filter rod circumference measurement. The circumference measurement and the pressure drop measurement may be noted by an operator and calculated in the manner to be described herein, or the two measurements may be appropriately fed as signals into a suitably programmed microprocessor to make the necessary calculations automatically.

Optical Measuring Instrument

Figure 3:
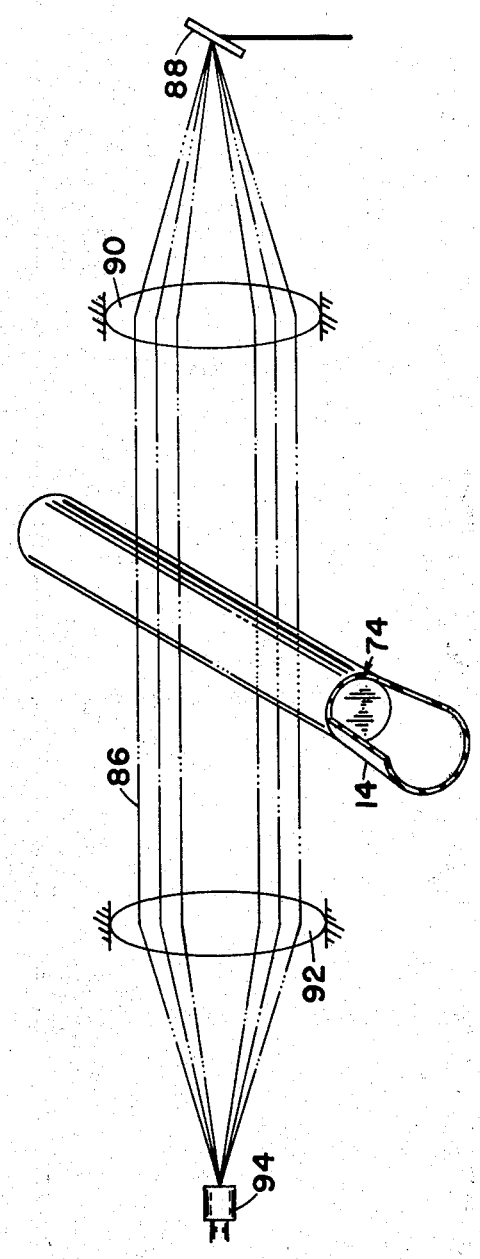
FIG. 3 is a schematic illustration of the optical measuring apparatus of FIG. 1; illustrating how the cigarette filter rod is measured by the optical measuring apparatus by means of the apparatus of the present invention.

In reference to FIG. 3, the cigarette filter rod 24 and the elastic sleeve 14 encapsulating it are shown positioned in the path of a parallel light scanning beam 86, which originates from a light source such as a laser (not shown). The light from the laser is reflected from a rotating mirror 88 and passes through a scanner lens 90, then passes over and under the filter rod and elastic sleeve and through a receiving lens 92 for subsequent receipt by a photodetector 94. The filter rod and elastic sleeve thus mask out or interrupt the light scanning beam. The blackout time or time interrupted by the article corresponds to the dimension of the filter rod and elastic sleeve. The parallel light scanning beam in effect, therefor, "sees" the substitute profile formed by the elastic sleeve around the filter rod. As the elastic sleeve and filter rod encapsulated therein are rotated, the substitute profile is then "read" by the optical measuring instrument to determine circumference.

Calibration Procedures

Initially, circumference measurement was evaluated without the tubular rubber diaphragm or elastic sleeve in place. A series of three metal standards, 24.11, 24.67 and 25.49 millimeters, were tested at 0.5 centimeter increments over the length of a 120 millimeter rod length (length of typical cigarette filter rods tested). This test was conducted to confirm that the optical measuring instrument 10 could measure a metal standard accurately over a 120 millimeter length. After thoroughly cleaning the optical glass plate 72, measurements were made over the entire 120 millimeter length. The results are tabulated in Table 1.

TABLE 1

| Test of Metal Standards - Without Elastic Sleeve | | | |
|---|---|---|---|
| | Metal Standard Circumference | | |
| Position (Centimeters) | 24.11 (Millimeters) | 24.67 (Millimeters) | 25.49 (Millimeters) |
| 0 (rear) | 24.11 | 24.67 | 25.50 |
| .5 | 24.11 | 24.67 | 25.49 |
| 1.5 | 24.10 | 24.68 | 25.50 |
| 2.0 | 24.11 | 24.68 | 25.50 |
| 2.5 | 24.11 | 24.67 | 25.50 |
| 3.0 | 24.12 | 24.67 | 25.49 |
| 3.5 | 24.11 | 24.68 | 25.49 |
| 4.0 | 24.11 | 24.67 | 25.50 |
| 4.5 | 24.10 | 24.67 | 25.50 |
| 5.0 | 24.11 | 24.67 | 25.49 |
| 5.5 | 24.11 | 24.68 | 25.50 |
| 6.0 | 24.12 | 24.68 | 25.50 |
| 6.5* | 24.11 | 24.67 | 25.49 |
| 7.0 | 24.12 | 24.68 | 25.50 |
| 7.5 | 24.11 | 24.67 | 25.50 |
| 8.0 | 24.12 | 24.68 | 25.50 |
| 8.5 | 24.11 | 24.67 | 25.50 |
| 9.0 | 24.11 | 24.68 | 25.49 |
| 9.5 | 24.10 | 24.67 | 25.49 |
| 10.0 | 24.11 | 24.67 | 25.50 |
| 10.5 | 24.11 | 24.67 | 25.49 |
| 11.0 | 24.11 | 24.68 | 25.49 |
| 11.5 | 24.10 | 24.67 | 25.50 |
| 12.0 (front) | 24.11 | 24.68 | 25.50 |

*Optical Measuring Instrument calibrated at point 6.5.

The data confirms that anomalies in the glass plates are not present and that a true circumference is measured at all points along the rod profile (without the elastic sleeve).

Figure 4:
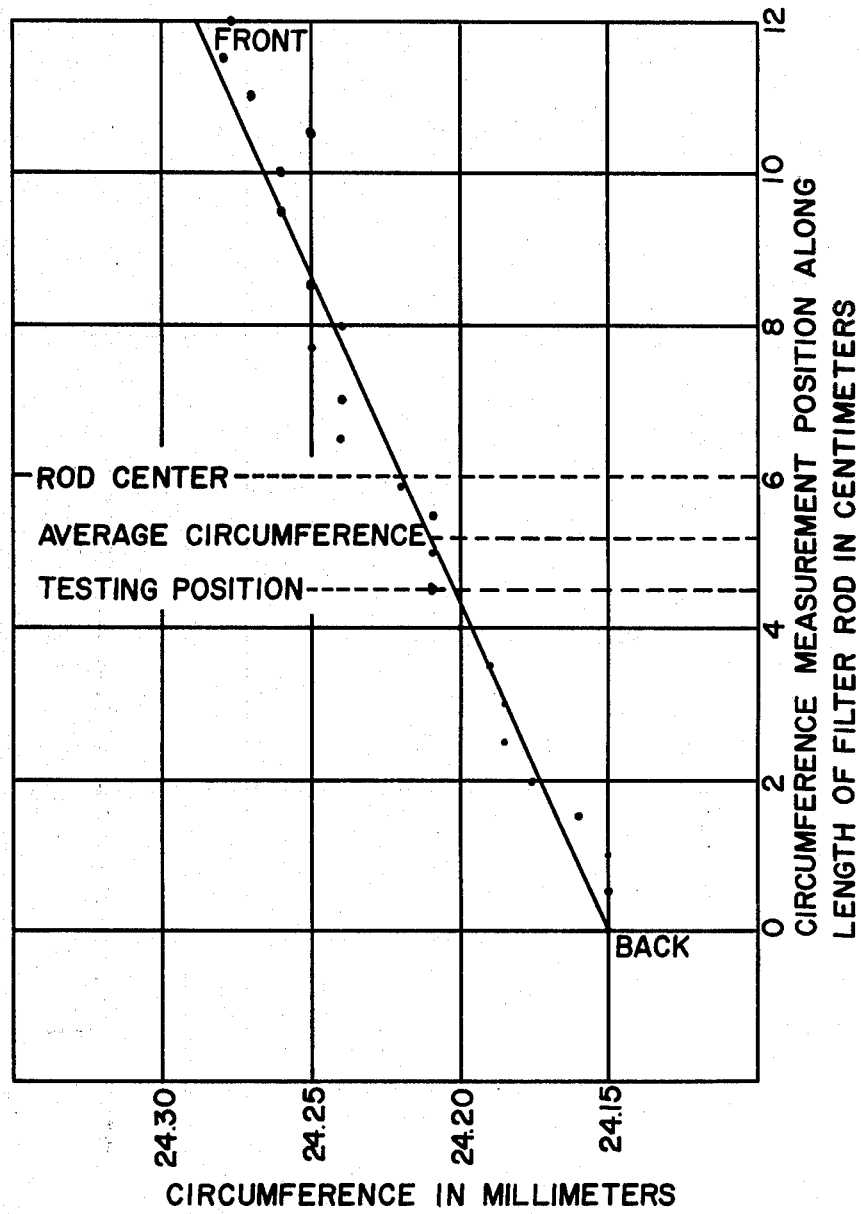
FIG. 4 illustrates a graph of a typical unwrapped cigarette filter rod profile inside of an encapsulating elastic sleeve.

For instance, position 0 is the end point at the rear of the chamber in FIG. 4; and position 12.0 is the end point at the front of the chamber, also in FIG. 4.

Figure 5:
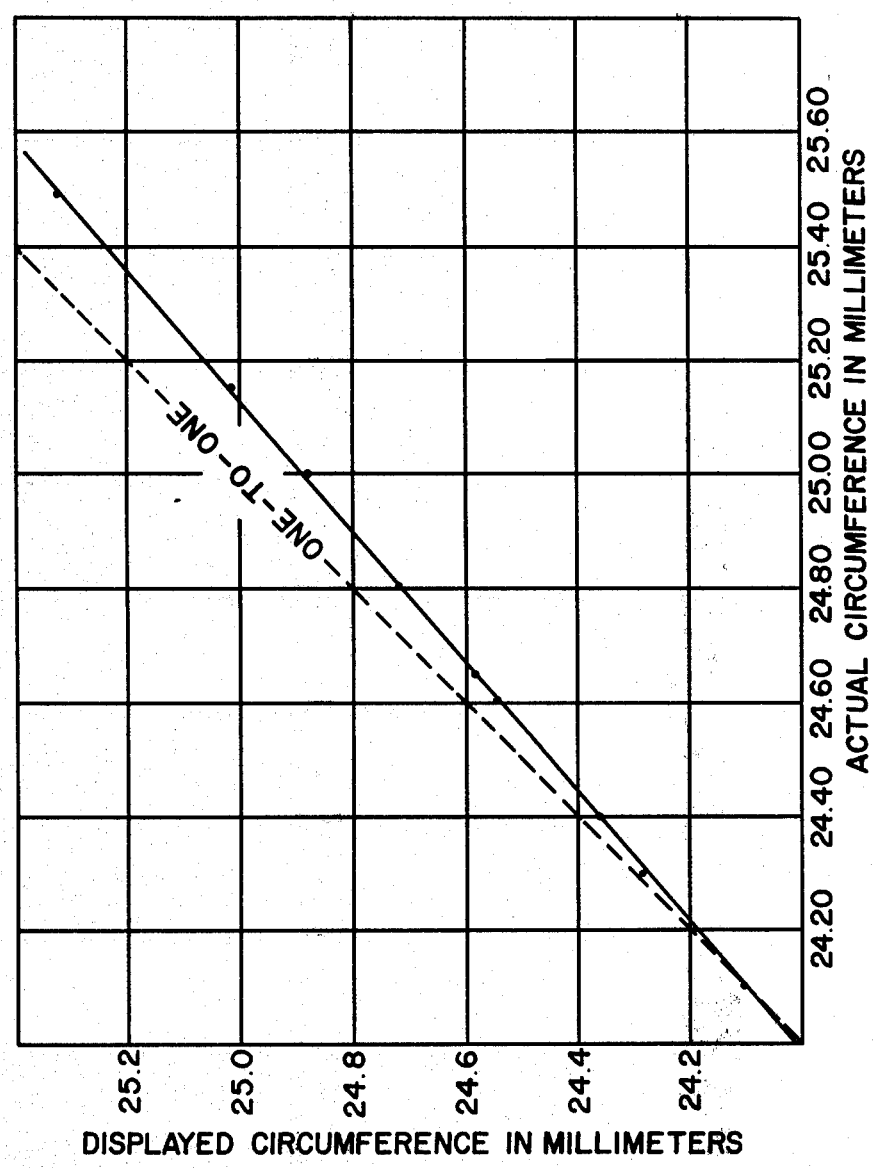
FIG. 5 illustrates a graph of actual versus displayed circumference using 5/16 inch Penrose tubing.

Next, the tubular rubber diaphragm or elastic sleeve was installed over the adjustable annular member 28 and secured with O-ring 34. It was found that the rear edge of the adjustable annular member 28 should be adjusted approximately 3 millimeters away from the particular filter rod length being tested so as to enable total encapsulation without pinching down the end of the filter rod. A range of circumference standards from 24.11 millimeters to 25.49 millimeters were inserted into the elastic sleeve and the displayed circumference was recorded. Using, for example, a 5/16 inch Penrose tubing (Penrose Latex Drainage Tubing, Manufactured by Davol, Inc., Providence, R.I.), the relation between actual circumference and displayed circumference was determined. The results are shown in FIG. 5. The relation is linear (and consistent for various 5/16 inch Penrose tubings) indicating the displayed circumference is less than actual when a larger circumference rod is tested. This occurs because of the rubber walls decreasing in thickness as the diaphragm is stretched by larger rods. Thus, the correction, with calibration being made at 24.11 millimeters, must be made to the displayed circumference to obtain actual circumference by the formula:

$$\text{Actual Circumference} = 1.141 \times \text{Displayed Circumference} - 3.40$$

The factors of 1.141 and −3.40 were determined by the statistical method of least squares curve fitting.

When an unwrapped filter rod is placed in an elastic sleeve and a vacuum flow applied to measure pressure drop, a varying radial force results along the length of the rod. The force is a function of both elastic force contributed by the elastic sleeve and the pressure differential along the rod due to the vacuum. This causes the rod to be compressed more on the rear section where the vacuum differential is greatest. By measuring the circumference profile of unwrapped filter rods inside the rubber sleeve, it was determined that the shape of the rods under test conditions is slightly conic. FIG. 4 shows a typical circumference profile of an unwrapped rod being tested, which generally showed about 0.15 millimeter difference (circumference) between the front and back of the 120 millimeter filter rod. The average circumference was found repeatedly to be about 0.5 centimeter to the rear of the rod center (toward the vacuum). Initial evaluations (to be discussed) indicated that the circumference measurement which produced consistently accurate results on a variety of rod specifications was 1.5 centimeters toward the rear of the rod center.

Pressure drop calibration was accomplished in a known manner by inserting a known laminar flow capillary and adjusting a needle valve in the pressure drop circuit. Routine calibration of both pressure drop and circumference can be accomplished by simply shuttling a laminar flow capillary tube through the apparatus, having previously determined its circumference at the point of measurement.

Evaluation Procedure

Because of the absence of any accepted standard method for judging the performance of the apparatus, a means of evaluation first had to be developed. This was accomplished through the use of unwrapped filter rods. The assumption was made that the pressure drop of a wrapped filter rod will be the same after removing the plugwrap, if the rod is not compressed. Thus, a sample of conventional rods may be tested for pressure drop, stripped of paper, tested for unwrapped circumference, and then tested on the apparatus. The unwrapped rods will, of course, be compressed in the apparatus and therefore will give an overstated pressure drop. However, by recording the compressed circumference and the accompanying pressure drop, a fifth power conversion equation may be employed to correct the pressure drop to the original unwrapped circumference level. If the principle of the instrument is sound, the corrected pressure drop and the original wrapped pressure drop should be the same. Further, the instrument should measure accurate pressure drop over a wide range of rod specifications. Thus, a number of sample variables were tested on the apparatus including hardness, rod length, circumference, and pressure drop range. Several different diaphragms were also tested.

Example of Fifth Power Conversion (1) Assume a nonwrapped filter rod of these specifications:

Circumference = 24.70 millimeters
Pressure drop = unknown ($\Delta P$ original)

(2) Upon measuring this filter rod on the apparatus of the invention, the compressed measurements are:

Measured circumference = 24.41 millimeters
Corrected to find actual circumference by taking
24.41 × 1.141 − 3.40 = 24.45
Actual circumference = 24.45 millimeters
Pressure drop = 16.53 inches of water (3) To obtain the original (uncompressed) pressure drop, the fifth power is used:

$$\Delta P \text{ original} = \left(\frac{24.45}{24.70}\right)^5 \times 16.53 \text{ inches of water} = 15.71 \text{ inches of water}$$

Establishment of Measuring Point

Because of the variable rod circumference during testing, a specific point along the rod length had to be chosen to obtain the compressed circumference reading. Ideally the point of average circumference should be used which was found to be 0.5 cm to the rear of the rod center (toward the vacuum source). Preliminary tests using the wrapped/unwrapped concept described above showed that good agreement was obtained when circumference was measured 1.5 centimeter to the rear of the rod center. Comparing the original to corrected pressure drop measured at the average circumferential point gave a corrected pressure drop of 0.3–0.4 inches higher than the wrapped pressure drop. Measurements were thus taken at the point 1.5 centimeter to the rear of the rod center. The above results were all based on a fifth power conversion. During the course of this project, results subsequently indicated that a sixth power pressure drop conversion yielded better agreement between experimental and theoretical curves. If one uses the sixth power conversion to correct pressure drop to original circumference, the point along the rod which gives the best agreement is the average circumference point. Therefore, if the sixth power conversion is to be used, circumference measurement on the apparatus should be carried out at the point 0.5 centimeter to the rear of rod center.

Results of Evaluation

A typical apparatus comparison of the wrapped rod and corrected unwrapped rod pressure drop values appears in Table 2. The wrapped circumference was initially determined by means of a spring-leaf assembly, as disclosed in my pending U.S. patent application Ser. No. 33,074, filed Apr. 25, 1979, now U.S. Pat. No. 4,213,707, issued July 22, 1980.

The spring-leaf assembly comprises two spring-loaded, stainless steel strips which ride on the upper and lower surfaces of the filter rod. As the filter rod is rotated, a laser beam scans the surface of the metal strips rather than the rod surface. The plugwrap was carefully removed from the rods. A measurement of unwrapped circumference was made on the apparatus (modified version) and consistently found to be 0.26 millimeter smaller than the wrapped rod circumference. The rods were then tested on the apparatus for pressure drop and circumference. This circumference, because of the rubber wall thickness changing, had to be corrected to the true circumference, in this example 24.67 millimeters. Thus, the measured pressure drop of 13.20 inches was converted using the fifth power conversion to a corrected pressure drop of 12.53 inches and using the original cellulose acetate rod circumference. The corrected pressure drop 12.53 compares to the original wrapped pressure drop of 12.59, well within the desired accuracy. On Table 3, a summary of the evaluations is listed. Ranges of rod specifications include:

Hardness—7.5 to 18.5 units
Circumference—24.34 to 24.95 millimeters
Wrapped Pressure Drop—10.79 to 21.30 inches
Rod Length—110 and 120 millimeters The comparison between original and corrected apparatus pressure drops are all well within desired accuracy. Several different diaphragms (all composed of the 5/16 Penrose tubing) were used during the evaluation and found not to bias the data in any manner. These results indicate that the apparatus very accurately measures pressure drop of an unwrapped rod if properly corrected from compressed circumference to the original (or nominal) circumference.

TABLE 2

| | Wrapped[1] Measured Circumference | Wrapped Δ P* (In inches of water) | Unwrapped[1] Measured Circumference | Unwrapped Δ P* (In inches of water) | Unwrapped Uncorrected Circumference | Unwrapped Corrected Circumference | Corrected Δ P* (In inches of water) |
|---|---|---|---|---|---|---|---|
| | TYPICAL APPARATUS COMPARISON (In Millimeters) | | | | | | |
| 1 | 25.20 | 12.92 | 24.94 | 13.58 | 24.59 | 24.64 | 12.78 |
| 2 | 25.21 | 11.94 | 24.95 | 12.56 | 24.62 | 24.67 | 11.87 |
| 3 | 25.22 | 12.80 | 24.95 | 13.47 | 24.64 | 24.70 | 12.50 |
| . | . | . | . | . | . | . | . |
| 18 | 25.18 | 13.03 | 24.92 | 13.67 | 24.59 | 24.64 | 12.92 |
| 19 | 25.25 | 11.92 | 24.98 | 12.51 | 24.66 | 24.72 | 11.87 |
| 20 | 25.23 | 12.66 | 24.96 | 13.25 | 24.63 | 24.68 | 12.52 |
| Average | 25.20 | 12.59 | 24.93 | 13.20 | 24.62 | 24.67 | 12.53 |

*Δ P = Pressure drop across length of the cigarette filter rod at a flow rate of 17.5 millimeters per second measured at exit end of filter rod.
[1] = Spring-leaf assembly measurements.

TABLE 3

SUMMARY OF APPARATUS EVALUATIONS
(In Millimeters)

| Test No. | No. Rods | Hardness[1] | Unwrapped[2] Circumference | Wrapped P | S.D. | Apparatus P | S.D.*** | Rod Length |
|---|---|---|---|---|---|---|---|---|
| 1 | 10 | 8.0 | 24.45 | 17.99 | .40 | 18.10 | .43 | 120 |
| 2 | 5 | 8.0 | 24.42 | 17.58 | .27 | 17.61 | .27 | 120 |
| 3 | 5 | 7.5 | 24.46 | 18.36 | .20 | 18.33 | .28 | 120 |
| 4 | 5 | 10.5 | 24.44 | 19.97 | .34 | 19.95 | .40 | 120 |
| 5 | 10 | 11.5 | 24.44 | 19.90 | .38 | 19.85 | .43 | 120 |
| 6 | 20 | 8.0 | 24.93 | 12.59 | .36 | 12.53 | .34 | 120 |
| 7 | 30 | 10.0 | 24.54 | 20.39 | .53 | 20.43 | .50 | 120 |
| 8 | 10 | 18.5 | 24.53 | 20.87 | .43 | 20.80 | .51 | 120 |
| 9 | 10 | 18.0 | 24.98 | 21.30 | .35 | 21.21 | .44 | 120 |
| 10 | 10 | 8.0 | 24.95 | 12.73 | .53 | 12.65 | .52 | 120 |
| 11 | 10 | 8.0 | 24.95 | 12.54 | .34 | 12.55 | .34 | 120 |
| 12 | 10 | 8.0 | 24.34 | 10.79 | .46 | 10.81 | .44 | 110* |
| 13 | 20 | 8.0 | 24.56 | 11.40 | .53 | 11.40 | .51 | 110** |

[1]Deflection in the filter rod measured in tenths of a millimeter times 10, when a weight of 411 grams is brought to bear on the side of a filter rod through a ¼-inch diameter platen for 10 seconds
[2]Spring-leaf assembly measurements
*Different elastic sleeve
**Tested on automated apparatus with different elastic sleeve
***S.D. = Standard deviation

Evaluation of Nonwrapped Filters Using The Apparatus

The final step in the evaluation consisted of testing actual nonwrapped rods with the indented surface that is characteristic of manufactured nonwrapped filter rods. To accomplish this, nonwrapped rods were tested on the apparatus to obtain compressed pressure drop and circumference. The rods were then wrapped in cellophane tape to prevent compression from occurring during retesting of pressure drop. This wrapped pressure drop was then compared to the corrected unwrapped pressure drop in a manner similar to the comparisons made with the conventional rods. The tape was applied with sufficient pressure to compress the surface of the rod and thereby eliminate leakage which might result in low pressure drop values. Results of this evaluation indicate that nonwrapped rod pressure drop can also accurately be measured on the apparatus.

Conclusions

The apparatus of the invention will measure the pressure drop of nonwrapped rods accurately within ±0.1 inch. The apparatus can easily be calibrated and is quite adaptable for an automated mode of testing. The instrument appears to be reliable over a wide range of filter rod specifications and is not biased by a change in diaphragms.

The invention has been described in detail with particular reference to certain preferred embodiments thereof, but it will be understood that variations and modifications can be effected within the spirit and scope of the invention.

I claim:

1. Apparatus for use with a gauging instrument, which measures and indicates the circumference of articles by means scanning the surface of the articles, and for determining in cooperation with said gauging instrument substantially true pressure drop measurement of nonwrapped and soft wrapped filter rods when the circumference of said filter rods is compressed for such pressure drop measurement by an encapsulation method, said apparatus comprising:

elastic sleeve means for receiving therewithin the entire length of a filter rod, and adapted to encapsulate said filter rod by close sealing adherence to and predetermined compression of the circumferential surface of said filter rod and thereby form a substitute profile on the profile of said filter rod, said substitute profile providing a reference surface to be measured;

means for supporting said elastic sleeve means in said apparatus;

means for generating a gas flow at a predetermined rate through said elastic sleeve means and through a filter rod encapsulated therein;

means for measuring and indicating the pressure difference at said predetermined flow rate between the flow of gas entering and the flow of gas leaving said filter rod; and means for rotating said elastic sleeve means while said gauging instrument measures said substitute profile circumference.

2. Apparatus as defined in claim 1, wherein said supporting means includes at the forward end of said elastic sleeve means an annular insertion guide means defining an opening through which a filter rod is inserted therethrough and into said elastic sleeve means, and also defining a radial outer surface around which said forward end of said elastic sleeve means is sealingly attached, and also includes at the rearward end of said elastic sleeve means an annular seat member against which said filter rod is seated while in said elastic sleeve means and defining a tapered radial outer surface around which said rearward end of said elastic sleeve means is sealingly attached, and also defining an opening through which said gas flow passes; said tapered radial outer surface of said annular seat member being tapered to about the same diameter of said elastic sleeve means, and said radial outer surface of said annular insertion guide means having a diameter greater than that of said elastic sleeve means and being spaced a predetermined distance from the filter rod so as to prevent pinching of the end of the filter rod.

3. Apparatus as defined in claim 2, wherein said radial outer surface of said annular insertion guide means is axially adjustable to accommodate different lengths of filter rods and correspondingly different lengths of elastic sleeve means.

4. Apparatus as defined in claim 1, wherein means is provided for defining an enclosed chamber within which said elastic sleeve means is supported, said chamber including means for expanding said elastic sleeve means to facilitate insertion therein of a filter rod, and including means for causing said filter rod to be moved into a predetermined position within said elastic sleeve means while said elastic sleeve means is expanded.

5. Method by which substantially true pressure drop measurement of nonwrapped and soft wrapped filter rods may be determined when the circumference of said filter rods is compressed for such measurement by an encapsulation method, said method comprising:

encapsulating the entire length of a filter rod in a gas impervious elastic sleeve, applying by said elastic sleeve a predetermined compression of the circumferential surface of said filter rod, and conforming said elastic sleeve in close sealing adherence to the surface of the circumferential profile of the filter rod to form a substitute profile on the profile of said filter rod, said substitute profile providing a reference surface to be measured;

generating a gas flow at a predetermined rate through said elastic sleeve and through a filter rod encapsulated therein;

measuring the pressure difference at said predetermined flow rate between the flow of gas entering and the flow of gas leaving said filter rod; and measuring the circumference of said substitute profile of said elastic sleeve.

6. The method as defined in claim 5, wherein said elastic sleeve and the filter rod encapsulated therewithin are rotated to obtain said substitute profile circumference measurement.

* * * * *